United States Patent [19]

Homma et al.

[11] 4,083,959

[45] Apr. 11, 1978

[54] THERAPEUTICAL METHOD FOR TREATING INFECTION OF MINK HEMORRHAGIC PNEUMONITIS

[75] Inventors: Yuzuru Homma, Tokyo; Takeshi Shimizu, Kodaira; Kazuo Okada, Tokyo, all of Japan

[73] Assignee: President of the University of Tokyo, Tokyo, Japan

[21] Appl. No.: 664,836

[22] Filed: Mar. 8, 1976

[30] Foreign Application Priority Data

Mar. 12, 1975  Japan ................................ 50-29104

[51] Int. Cl.$^2$ ............................................. A61K 39/02
[52] U.S. Cl. ..................................................... 424/92
[58] Field of Search ........................................... 424/92

[56] References Cited

U.S. PATENT DOCUMENTS

3,928,565  12/1975  Homma et al. ..................... 424/92

OTHER PUBLICATIONS

The Merck Veterinary Manual–4th Ed. (1973) pp. 809–810.

Primary Examiner—Sam Rosen
Attorney, Agent, or Firm—Blum, Moscovitz, Friedman & Kaplan

[57] ABSTRACT

A therapeutic preparation of a bacterial component (designated as OEP and formally as CWP) derived from *Pseudomonas aeruginosa* possesses vaccine activity (the effective component being a lipoprotein of *Pseudomonas aeruginosa*) or the same containing antibiotics is effective in the treatment of mink hemorrhagic pneumonitis and bovine mastitis due to *Pseudomonas aeruginosa*.

1 Claim, No Drawings

THERAPEUTICAL METHOD FOR TREATING INFECTION OF MINK HEMORRHAGIC PNEUMONITIS

BACKGROUND OF THE INVENTION

*Pseudomonas aeruginosa* is known to be naturally resistant against most of antibiotics commonly used. Although there are only a few antibiotics to which the bacteria are sensitive, the use of these antibiotics in the therapy of infections due to *Pseudomonas aeruginosa* is not effective in most cases when the hosts are physiologically immature in immune response or in these cases in which the hosts are being treated by administration of medicines which deteriorate their immune mechanisms.

Mink infection due to *Pseudomonas aeruginosa* is well known as a so-called hemorrhagic pneumonitis. For the purpose of protecting mink from this contagious disease, minks were usually immunized with the formalin-killed bacteria which had been isolated from mink killed by the endemic disease. However, the effect of this vaccine has been doubtful. Therapy by means of antibiotics effective against the bacteria is usually not applicable, because its administration for only a few times is insufficient for preventing the natural development of the endemic disease, and repeated administrations at 2–3 day intervals are impossible. Generally speaking, there are thousands of minks in one farm and only special technicians can manage the vaccination of the mink. The high cost of the drugs is another reason for the unsuitability of antibiotics for this purpose.

As to bovine mastitis, there was a case in which antibiotics were administered continuously, but the cost involved was excessive. An acute case may be treated with antibiotics, but most chronic cases can hardly be treated in this way.

The radical treatment of mastitis infected by *Pseudomonas aeruginosa* could not be achieved by antibiotics alone because of the recurrence of infection after the temporary success of the treatment.

The formalin-killed vaccine used so far is also unsatisfactory in that this vaccine is merely capable of preventing or treating infection by the same homologous serotype strain as that from which the vaccine was derived. Since more than 13 kinds of serotype (O antigen) are known in *Pseudomonas aeruginosa* and a specific O antigen can protect animals only against infection by the homologous O serotype strain, this particular vaccine cannot be prepared in advance for prophylactic (therapeutical) purposes. Once there occurs the endemic disease due to *Pseudomonas aeruginosa*, approximately 30–50% minks in a farm die because of hemorrhagic pneumonitis.

On the other hand, it has been proved that an immune state of a host is a very important defense factor against infection due to *Pseudomonas aeruginosa*. As for immunotherapy using vaccine and plasma against *Pseudomonas aeruginosa* infection, there have been published many papers, reporting that both active and passive immunization are effective against *Pseudomonas aeruginosa* in certain types of infection caused by the bacillus. The lipopolysaccharide (LPS) derived from *Pseudomonas aeruginosa* is protective only against infection with the same serotype strain as that from which it is derived. Therefore, several several LPSs had to be admixed in order to develop a vaccine for use against all the types of *Pseudomonas aeruginosa* infection.

The present invention is based upon the finding that the component OEP consisting mainly of protein is capable of preventing infection by all the serotype strains belonging to *Pseudomonas aeruginosa*.

SUMMARY OF THE INVENTION

A therapeutic preparation comprised principally of a lipoprotein of *Pseudomonas aeruginosa* is proved to have vaccine activity against hemorrhagic pneumonitis of mink and bovine mastitis due to *Pseudomonas aeruginosa*. In addition to lipoprotein, the vaccine contains a small amount of a lipid and a sugar also derived from the *Pseudomonas aeruginosa* bacteria. The effectiveness of the vaccine is enhanced by the addition of one or more of the antibiotics, Panimycin, Colistin, Gentamycin, Polymixin, Carbenicillin, Sulbenicillin and Cephalothin.

In the therapeutic treatment of mink hemorrhagic pneumonitis and bovine mastitis by *Pseudomonas aeruginosa*, the dosage of a preparation consisting mostly of the protein of *Pseudomonas aeruginosa* should lie between 5 and 500 $\mu$g/kg for mink and 0.3 and 50 $\mu$g/kg for cattle.

During the dry season, it is preferred that the therapeutic preparation be injected into the nipples or into any part of the body including the breasts, intramuscularly.

Accordingly, an object of the present invention is to provide a therapeutical preparation for the treatment of mink hemorrhagic pneumonitis and bovine mastitis infected with *Pseudomonas aeruginosa*.

Another object of the present invention is to provide a method of treating mink infection and bovine mastitis caused by *Pseudomonas aeruginosa*.

Still other objects and advantages of the invention will in part be obvious and will in part be apparent from the specification.

The invention accordingly comprises the several steps and the relation of one or more of such steps with respect to each of the others, and the composition possessing the features, properties, and the relation of constituents which are exemplified in the following detailed disclosure, and the scope of the invention will be indicated in the claims.

DETAILED DESCRIPTION OF THE PREFERRED EMBODIMENTS

The present invention provides a therapeutical preparation for mink infection and bovine mastitis due to *Pseudomonas aeruginosa*, the effective component being OEP which possesses vaccine activity. The component OEP is obtained by the method described in British patent specification No. 1,365,950 published Sep. 4, 1976. The material identified in said patent as CWP is equivalent of the OEP referred to herein.

The invention also provides a method of administering a therapeutical preparation mainly composed of OEP to mink and cattle for the purpose of treating an infective disease caused by *Pseudomonas aeruginosa*.

The vaccine activity of OEP provides protection against infection by *Pseudomonas aeruginosa* regardless of the serotype of the *Pseudomonas aeruginosa;* this OEP possesses in addition to its non-specific protection against infection due to *Pseudomonas aeruginosa*, protection against other bacteria. It also has antitumor and interferon-inducing (I.F.) activities.

OEP, an effective component of therapeutic preparation referred to in the present invention, could be obtained by isolating the protein fraction of *Pseudomonas aeruginosa*, but does not contain, in principle, O antigen involved in the so-called endotoxin LPS, and is therefore essentially different from the thermostable O antigen (LPS) referred to heretofore.

The following is an example showing a chemical analysis of OEP:

| | |
|---|---|
| N | 13.8% |
| P | 1.17 |
| Anthrone | 0.01 |
| Hexosamine (Elson-Morgan) | 0.03 |
| KDO | 0.3 |
| Protein | 85% |

The following is an example indicating the amino acid content of OEP protein:

| | |
|---|---|
| Glycine | 5.2% (mol) |
| Alanine | 8.7 |
| Valine | 6.9 |
| Leucine | 9.8 |
| Isoleucine | 5.1 |
| Serine | 4.0 |
| Threonine | 4.9 |
| Tyrosine | 3.8 |
| Phenylalanine | 4.7 |
| Methionine | 2.3 |
| Proline | 4.0 |
| Asparagine | 9.1 |
| Glutamine | 14.3 |
| Histidine | 2.4 |
| Arginine | 6.7 |
| Lysine | 7.4 |

A therapeutic preparation mainly composed of OEP can be prepared, for instance, by adding known diluents such as phosphorous buffer solutions and the like. OEP alone can be employed for the treatment, but is more effective when combined with antibiotics such as Gentamycin, Panimycin, Colistin, Polymixin, Sulbenicillin, Carbenicillin and Cephalothin.

When the above therapeutic preparation is administered to mink, OEP is the basic dose to be given in an amount of 5 to 500 μg/kg together with either KA (potassium alum) or FIA (Freund's Incomplete Adjuvant) for 1 or 2 days at 1 to 4 week intervals.

The drug can be given repeatedly as well, or a single dose of 5 to 1,000 μg/kg unaccompanied with KA or FIA can also be administered on the third day. There is no limit to the number of administrations, but both the dose and the number of days for administration must be adjusted so that a sufficient antigenic value is obtained, as indicated by the OEP-hemagglutination test (the OEP-HA test), and the administration can be discontinued when the expected value is obtained. However, as is described hereabove, a sufficient result is achieved in most cases when the dose is given twice. OEP is also the basic dose to be given for bovine infection and a daily dose of 0.3–50 μk/kg is repeatedly administered at a few days' intervals, but an amount to be continuously administered must be such that does not cause pyrexia or any other side-effects. Although the OEP-HA value is not involved in this case, the aforementioned antibiotics are preferred to be combined with OEP for the therapeutical treatment.

The following Examples serve to illustrate the invention.

EXAMPLE 1

Therapy for treatment of mink infection caused by *Pseudomonas aeruginosa*

When minks are infected by *Pseudomonas aeruginosa*, they soon becomes less energetic and gloomy and reject all food. A day or a few days thereafter, they minks die of hemorrhagic pneumonitis and septicaemia accompanied with hemoptysis.

In autumn 1974, OEP was first employed for the field work treatment of an endemic outbreak of mink hemorrhagic pneumonitis due to *Pseudomonas aeruginosa* on the biggest scale ever encountered in Japan. For reliable evaluation of the therapeutic effect of OEP, half of the infected minks should have been left as controls without inoculating them, but owing to the extreme prevalence of the contagious disease, it was imperative to inoculate all the minks subcutaneously with OEP at a dosage of 25 μg–375 μg each. The inoculation was repeated twice or three times. Strains of *Pseudomonas aeruginosa* isolated from internal organs of dead minks were found to belong to Homma's serotype 8, while the OEP antigen used was derived from the strain belonging to serotype 5.

The number of mink deaths classified by the mink farm before and after the inoculation with OEP are shown in Table 1.

Table 1

| Farm No. | Number of Mink Deaths Before and After Inoculation with OEP | | | | | | | | | |
|---|---|---|---|---|---|---|---|---|---|---|
| | −13−−7 | vaccination ↓ −6−0 | 1–7 | 8–14 | 15–21 | 22–28 | 29–35 | 36–42 | 43–49 | 50–56 |
| 6 | 38 | 290 | 238 | 13 | 1 | 1 | 0 | 0 | 0 | 0 |
| 7 | 3 | 9 | 202 | 257 | 20 | 0 | 0 | 0 | 0 | — |
| 1 | 0 | 2 | 20 | 33 | 14 | 0 | 0 | — | — | — |
| 2 | 0 | 0 | 0 | 1 | 31 | 20 | 39 | 21 | 5 | — |
| 3 | 0 | 1 | 1 | 170 | 35 | 35 | 15 | 7 | — | — |
| 4 | 0 | 2 | 2 | 169 | 37 | 11 | 3 | 4 | — | — |
| 5 | 0 | 0 | 0 | 1 | 2 | 3 | 1 | 1 | 0 | 0 |

In Table 1, −13 means 13 days before the inoculation with OEP. The number of minks at each farm is given in Table 2 below. The number at farm No. 6 was 1240.

On the 7th day after the OEP inoculation, OEP-HA titers (reciprocal of the tested serum dilution) in sera of mink were found to be from 80 to 620 times, (all while those in sera before inoculation were all negative). Consequently, evaluation of results was done on the assumption that therapeutical effect of OEP vaccination should be observed at least on the 8th day after the first administration, even though it was slight.

Of all the 7 mink farms, the current infection was first discovered in No. 6 where the mortality was highest. The inventors have taken the mortality reported up to the 7th day after the OEP inoculation as the death rate to be expected in the absence of OEP treatment and have postulated that an equivalent number of minks, namely 45.2% of them being bred in other farms, would have died if untreated. Thus, Table 2 shows the therapeutic effect of OEP indicated by a ratio expressed in percent between the number of minks considered to have survived as a result of the inoculation with OEP and the number of minks expected to die in the absence of treatment with OEP.

production of milk and inactive gait in most cases; their breasts then get indurated producing bloody or yellowish cream-colored milk. After some chronic conditions, cows finally die with either endotoxin or necrosis.

TABLE 2

THERAPEUTICAL EFFECT OF OEP

| Farm No. | No. of minks being bred | No. of dead minks | No. of minks expected to die when without OEP treatment | No. of minks considered to survive as the result of OEP treatment | Therapeutic effect of OEP - $(\frac{**}{*}) \times 100$ |
|---|---|---|---|---|---|
| 6 | 1240 | 581 | | | |
| 7 | 1208 | 491 | 544 | 53 | 9.7 |
| 1 | 710 | 69 | 319 | 250 | 78.4 |
| 2 | 1351 | 117 | 607 | 490 | 80.7 |
| 3 | 1150 | 316 | 517 | 201 | 38.8 |
| 4 | 1000 | 299 | 450 | 151 | 33.6 |
| 5 | 936 | 10 | 421 | 411 | 97.6 |

* The number of dead minks (566) in No. 6 farm (— 13 – 7th day). The number of minks being bred in No. 6 farm (1240) = 0.452. On the assumption that the minks would die in a ratio obtained by the above formula, the calculation was made by multiplying the number of minks being bred in each farm by 0.452.
** The number of minks being bred in each farm × 0.452 - the number of dead minks in each farm.

The therapeutic effect was only 9.7% at the No. 7 farm but it represented 78.4%, 80.7%, 38.8%, 33.6% and 97.6% at farms Nos. 1, 2, 3, 4 and 5 respectively.

Next, the calculation based upon the assumption that OEP would exhibit its therapeutic effect from the 15th day after inoculation has revealed an increasing effect in each farm amounting to 13.4% with No. 7 farm, and 79.2%, 81.5%, 41.2%, 37.7% and 97.7% with farm Nos. 1, 2, 3, 4 and 5 respectively.

In investigations carried out on the surviving minks, *Pseudomonas aeruginosa* was not isolated from any of them and no pathological changes were recognized.

However, when administered repeatedly for such conditions of mastitis, OEP demonstrates a significant effect regardless of the serotype of the infecting organisms. When combined with antibiotics, OEP can be still more effective in the therapeutic treatment, and the following is one of such examples.

In Spring 1974, there was a mass outbreak of mastitis caused by *Pseudomonas aeruginosa* at one of the cow breeding farms in Chiba Prefecture, Japan, and a few cows died. OEP combined with antibiotics was then administered to three severely affected cows immediately thereafter. The dose given is detailed in Table 3.

TABLE 3

THERAPY SCHEDULE IN TREATMENT OF MASTITIS CAUSED BY PSEUDOMONAS AERUGINOSA

| Medication Day | No. 1 Cow | | | No. 2 Cow | | No. 3 Cow | |
|---|---|---|---|---|---|---|---|
| | OEP | GM* | CB-PC** | OEP | CB-PC | OEP | CB-PC |
| 1 | 0.5mg (Br.S.) | 80mg × 3 (Mus.) | 300mg × 1 (Br.) | 0.5mg (Br.S.) | 300mg × 1 (Br.) | 0.5mg (Br.S.) | 300mg × 1 (Br.) |
| 2 | " | 40mg × 2 " | 300mg × 1 " | | 300mg × 1 " | | 300mg × 1 " |
| 3 | 0.7mg " | | | 0.7mg " | " | 0.7mg " | |
| 6 | 1.0mg " | | | 1.0mg " | | 1.0mg " | |
| 8 | | 80mg × 3 " | 300mg × 1 " | | 300mg × 1 " | | 300mg × 1 " |
| 9 | 1.7mg " | 40mg × 2 " | 300mg × 1 " | 1.7mg | 300mg × 1 " | 1.7mg " | 300mg × 1 " |
| 12 | 2.5mg (Mus.) | | | 2.5mg (Mus.) | | 2.5mg (Mus.) | |
| 15 | 5mg " | 80mg × 3 " | 300mg × 1 " | 5mg " | 300mg × 1 " | 5mg " | 300mg × 1 " |
| 16 | | 40mg × 2 " | 300mg × 1 " | | 300mg × 1 " | | 300mg × 1 ") |
| 21 | 10mg " | | | 10mg " | | 10mg " | |
| 22 | | 80mg × 3 " | 300mg × 1 " | | 300mg × 1 " | | 300mg × 1 " |
| 23 | | 40mg × 2 " | 300mg × 1 " | | 300mg × 1 " | | 300mg × 1 " |
| 27 | 20mg " | ) | 25mg " | | 25mg " | | " |

Note:
*GM = Gentamycin
**CB-PC = Carbenicillin
Br.S. = injected into breasts subcutaneously
Mus. = injected muscularly
Br. = injected into breasts

EXAMPLE 2

Therapy for bovine mastitis caused by *Pseudomonas aeruginosa*

When the mammary region is infected by *Pseudomonas aeruginosa*, cows present, in the first place, such symptoms as pyrexia and swelling of breasts, drop in As a result of the treatment, most symptoms had disappeared in all cases, and no side-effects attributable to the OEP inoculation were recognized. When No. 2 cow was killed for the autopsy in the second month after the medication was terminated, a slight swelling was noted only in the right posterior breast. According to the autopsy, every organ, third breasts and 9 months' fetus were equally proved normal. Although partial hypertrophy of connective-tissue membrane of the right posterior breasts was recognized, no bacilli were detected in any of the fourth breasts.

No. 3 cow delivered a normal fetus in the third month after the termination of medication. Autopsy carried out 1 month thereafter revealed no significant abnormality in any of the organs, but a growth was found in the connective-tissue membrane of the second breasts. However, not a single strain was detected in any of the fourth breasts.

The serum OEP-HA values obtained on the day prior to the OEP inoculation and 33 days thereafter were 640 and 10,240 times in a case with No. 1 cow, 1,280 and 1,280 times with No. 2 and 2,560 and 10,240 times with No. 3, respectively.

As is evident from these two series of tests, OEP is an effective therapeutic agent in the treatment of mink hemorrhagic pneumonitis and bovine mastitis.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Therapeutic method of treating mink infection caused by *Pseudomonas aeruginosa*, comprising the steps of administering 5 to 500 $\mu$g/kg of a therapeutic preparation mainly composed of protein of *Pseudomonas aeruginosa* having vaccine activity to mink.

* * * * *